United States Patent
Yang et al.

(12) 
(10) Patent No.: US 6,270,722 B1
(45) Date of Patent: Aug. 7, 2001

(54) STABILIZED BROMINE SOLUTIONS, METHOD OF MANUFACTURE AND USES THEREOF FOR BIOFOULING CONTROL

(75) Inventors: Shunong Yang; William F. McCoy, both of Naperville; Eric J. Allain, Aurora; Eric R. Myers, Aurora; Anthony W. Dallmier, Aurora, all of IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/283,122

(22) Filed: Mar. 31, 1999

(51) Int. Cl.[7] ............................... A61L 2/16; C01B 7/09; D06L 3/06
(52) U.S. Cl. ................................ 422/37; 422/6; 8/107; 8/137; 162/1; 423/500; 252/187.2
(58) Field of Search ................................ 422/37, 6, 14; 8/107, 137; 162/1, 4; 423/500, 504; 252/187.2, 380

(56) References Cited

U.S. PATENT DOCUMENTS

| | | |
|---|---|---|
| 3,328,294 | 6/1967 | Self et al. . |
| 3,558,503 | 1/1971 | Goodenough et al. . |
| 3,767,586 | 10/1973 | Rutkiewic et al. . |
| 5,683,654 | 11/1997 | Dallmier et al. . |
| 5,795,487 | 8/1998 | Dallmier et al. . |
| 6,007,726 * | 12/1999 | Yang et al. .................. 422/37 X |
| 6,015,782 * | 1/2000 | Petri et al. .................. 510/379 |
| 6,110,387 * | 8/2000 | Choudhury et al. .......... 210/752 |

FOREIGN PATENT DOCUMENTS

| | | |
|---|---|---|
| WO 97/20909 | 6/1997 | (WO) . |
| WO 97/43392 | 11/1997 | (WO) . |

\* cited by examiner

*Primary Examiner*—Elizabeth McKane
(74) *Attorney, Agent, or Firm*—Kelly L. Cummings; Thomas M. Breininger

(57) ABSTRACT

Stabilized bromine solutions are prepared by combining a bromine source and a stabilizer to form a mixture, adding an oxidizer to the mixture, and then adding, an alkaline source to adjust the pH of the mixture to at least 13.

30 Claims, No Drawings

STABILIZED BROMINE SOLUTIONS, METHOD OF MANUFACTURE AND USES THEREOF FOR BIOFOULING CONTROL

FIELD OF THE INVENTION

This invention relates generally to water treatment and, more particularly, to stabilized bromine solutions, method of manufacture and uses thereof for biofouling control.

BACKGROUND OF THE INVENTION

Sodium hypochlorite has been widely used in a variety of industrial and recreational water systems to control biofouling. However, sodium hypochlorite is unstable and must be provided in a stabilized form. There are several methods known in the art for stabilizing hypochlorite (See, e.g., U.S. Pat. Nos. 3,328,294 and 3,767,586).

Bromine is preferred over chlorine for use in water treatment because of its lower volatility and better performance at high pH and amine environments. However, like sodium hypochlorite, sodium hypobromite is unstable in typical storage conditions and must therefore also be provided in a stabilized form. U.S. Pat. Nos. 5,683,654 and 5,795,487, as well as the references disclosed therein, teach various methods for stabilizing sodium hypobromite. The '654 and '487 patents disclose batch methods which utilize sodium hypochlorite and sodium bromide as starting materials, followed by the addition of a stabilizer. WO 97/20909 similarly discloses a process which includes a hypobromite formation step followed by a bromine stabilization step. However, a disadvantage associated with this technique is that unstabilized hypobromite is formed in a separate step at a high concentration and pH. It is known that unstabilized hypobromite degrades quickly under such conditions to form bromate, a non-biocidal compound that is very toxic and a suspected carcinogen.

In addition, WO 97/43392 discloses a process that first forms stabilized chlorine compounds and then converts them to stabilized bromine compounds. However, this type of process is limiting because only hypochlorite-releasing compounds can be used as the oxidizing source.

Therefore, because the demand for stabilized bromine solutions is expected to increase in the future due to its advantages over chlorine, there is a need for other cost-effective methods of manufacturing stabilized bromine which can use a wider range of oxidants and produce a higher strength product at higher yield.

Accordingly, it would be desirable to provide a method of making a stabilized bromine solution which can be carried out as a batch or continuous process and which can produce a higher strength product at higher yield. It would also be desirable to develop a method of making a stabilized bromine solution which is flexible and allows a variety of oxidizers to be utilized.

SUMMARY OF THE INVENTION

The stabilized bromine solutions of the present invention are prepared by combining a bromine source and a stabilizer to form a mixture, adding an oxidizer to the mixture, and then adding an alkaline source to adjust the pH of the mixture to at least 13.

The inventive method is economically appealing because it can be carried out as a batch or continuous process and because it produces a high-strength stabilized bromine solution at higher yield. The method of preparation is also flexible and allows for the utilization of a variety of oxidizers.

DETAILED DESCRIPTION OF THE INVENTION

The present invention is directed to a method of making stabilized bromine solutions. In accordance with this invention, a bromine source and a stabilizer are combined to form a mixture, an oxidizer is next added to the mixture and then an alkaline source is added to adjust the pH of the mixture to at least 13.

The bromine sources which may be used in the practice of the present invention include hydrobromic acid, bromine chloride, elemental bromine and alkali or alkaline earth metal bromides, such as sodium bromide, potassium bromide and lithium bromide.

The stabilizers which may be employed in this invention have the chemical formula $R-NH-R^1$, wherein $R$ and $R^1$ are selected from the group consisting of $R^2$ CO, $R^2$ $SO_2$, $R^2$ $CF^2$, $R^2$ CHF, H, OH and $PO(OH)_2$, and $R^2$ is an alkyl group or an aromatic group. Suitable stabilizers include saccharin, urea, thiourea, creatine, cyanuric acids, alkyl hydantoins, monoethanolamine, diethanolamine, organic sulfonamides, biuret, sulfamic acid, organic sulfamates and melamine. Sulfamic acid is the most preferred stabilizer.

The oxidizers which may be used include chlorine gas, hypochlorous acid, hypochlorite salt, chlorite, chlorate, elemental bromine, bromine chloride, hydrogen peroxide, persulfate, permanganate and peracetic acid. It is believed that other peroxy compounds can also be used in accordance with this invention.

The alkaline source is preferably an alkali or alkaline earth metal hydroxide. Suitable alkaline sources include sodium hydroxide, lithium hydroxide, potassium hydroxide, magnesium hydroxide and calcium hydroxide.

It is preferred that the molar ratio between the bromine source and the stabilizer be in the range of about 0.2 to 5. The molar ratio between the bromine source and the oxidizer should preferably be in the range of about 0.5 to 2.

The method of the present invention is maintained at a temperature of less than 80° F., and preferably in the range of about 40 to 70° F. The pH of the mixture during the oxidizer addition should be kept below about 7. The present invention can be carried out as either a batch or continuous process.

The stabilized bromine solutions which are prepared in accordance with this invention may be used in a wide variety of commercial applications. These applications include, but are not limited to, the use of the stabilized bromine solution: (1) as the bleaching agent in a method for the laundering of soiled garments in which the soiled garments are washed in an aqueous media containing a detergent and a bleaching agent; (2) as the oxidizing agent in a method for the manufacture of cellulosic materials in which cellulosic fibers are bleached; (3) as the oxidizing and biocidal agent in a method for the control of biofouling in a recreational water system in which an oxidizing and biocidal agent is added to control biofouling; (4) as the oxidizing and biocidal agent in a method for the control of biofouling on a hard surface in which an oxidizing and biocidal agent is applied to the surface to control biofouling on the surface; (5) in a method for the control of biofouling occurring on the surfaces of equipment in contact with produced oil field waters; and (6) in a method for controlling biofouling in an aqueous system.

In another embodiment, the invention is a method of preventing biofouling on the surfaces of equipment in contact with an industrial water system. The method comprises adding an effective biofouling controlling amount of a stabilized bromine solution to the water system, wherein the solution is prepared by combining a bromine source and a stabilizer to form a mixture, adding an oxidizer to the mixture, and then adding an alkaline source to adjust the pH of the mixture to at least 13.

The types of industrial water systems in which the stabilized bromine solution may be used to prevent biofouling include, but are not limited to, cooling water systems, sweetwater systems, gas scrubber systems, air washer systems, evaporative condensers, pasteurizers, produce sanitizer streams, fire protection water systems and heat exchanger tubes.

It is preferred that the amount of stabilized bromine solution which is added to the industrial water system be in the range of about 0.1 ppm to about 2000 ppm and preferably in the range of about 0.5 ppm to about 500 ppm, based on available bromine concentration. The stabilized bromine solution can be added to the water system by any conventional method, i.e., by slug, intermittently or continuously.

In another embodiment, the invention is a method of making a stabilized bromine solution comprising the steps of selecting a bromine source, and then adding a stabilizer and an oxidizer to the bromine source to form a mixture, wherein the stabilizer and the oxidizer are alternately added to the mixture in an amount sufficient to maintain the pH of the mixture between about 0 and 6.9, more preferably between about 3 and 6.5 and, most preferably, between about 4 and 6. Those skilled in the art will recognize that the amount of stabilizer and oxidizer added can be determined by automatic feed back control based on the pH value of the mixture or simply done manually. At the end of stabilizer and oxidizer addition, an alkaline source is added to the mixture to adjust the pH of the mixture to at least 13. It is preferred that the molar ratio between the bromine source and the stabilizer be in the range of about 0.2 to 5. The molar ratio between the bromine source and the oxidizer should preferably be in the range of about 0.5 to 2. All of the suitable bromine sources, stabilizers, oxidizers and alkaline sources which may be used in accordance with this embodiment of the invention, as well as the temperature conditions, are the same as those described above.

EXAMPLES

The following examples are intended to be illustrative of the present invention and to teach one of ordinary skill how to make and use the invention. These examples are not intended to limit the invention or its protection in any way.

Example 1

A bench scale experiment was conducted by:
a. mixing 6.83 grams of a 45% sodium bromide solution with 3.30 grams of solid sulfamic acid in a 250 ml flask and then immersing the flask in an ice-water bath;
b. slowly adding 47.5 grams of a 4.0% sodium hypochlorite solution to the flask while shaking the flask inside the ice-water bath to maintain a low enough temperature so that no bubbling could be seen; and
c. slowly adding 4.5 grams of a 50% sodium hydroxide solution to the flask while cooling the flask.

The resulting product was an amber color solution with a pH of 13.5 and total halogen concentration of 6.89% as $Br_2$ (or 3.06% as available chlorine) as measured by potassium iodide-sodium thiosulfate titration. The ultraviolet (UV) spectra of the product were typical of a stabilized bromine pattern. The free and total DPD calorimetric measurements also suggested that the product was mostly oxidizing bromine compounds (~98%).

Example 2

The same process performed above in Example 1 was used to make a higher concentration product using industrial grade sodium hypochlorite in a lab scale.

The product was prepared by:
a. mixing 20.5 grams of a 45% sodium bromide solution with 8.70 grams of solid sulfamic acid in a 200 ml flask and then immersing the flask in an ice-water bath to keep the temperature low;
b. slowly adding to the mixture 44.0 grams of 14.2% (w/w as available chlorine) industrial grade sodium hypochlorite while shaking the flask in the ice-water bath; and
c. adding 12.2 grams of a 50% sodium hydroxide solution to the mixture.

The resulting product was an amber color solution with a pH of 13.5 which contained 15.91% as $Br_2$ (or 7.07% as available chlorine) according to potassium iodide-sodium thiosulfate titration. The UV spectra of its 1,000 fold dilution were typical of a stabilized bromine profile. The free and total DPD colorimetric measurements also suggested that the product was 100% oxidizing bromine compounds.

Example 3

The inventive method was also tested using an in-line approach. Bromine was oxidized and stabilized in a continuous set-up. The process started by preparing two solutions (A and B) in two separate flasks. Solution A was prepared by mixing 60.9 grams of solid sulfamic acid and 143.5 grams of 45% (w/w) sodium bromide solution. Water was added to bring the total volume of Solution A to approximately 375 milliliters. Solution B was prepared by diluting 313.4 grams of 14.2% (w/w as chlorine) sodium hypochlorite with water to 375 milliliters. Solutions A and B were then pumped out of the flasks at a rate of approximately 19 milliliters per minute using a dual pump-head peristaltic pump. The two solutions were blended through a T-tubular connector immersed in an ice-water bath. The mixed solution then traveled through forty feet of ⅛ inch inner diameter PVC tubing immersed in the water bath before discharging into another flask which contained 85.4 grams of 50% (w/w) sodium hydroxide solution.

The resulting product had a total weight of 927 grams. The product had a pH of more than 13.5 and 9.07% as Br, (or 4.03% as available chlorine) as measured by potassium iodide-sodium thiosulfite titration. The UV spectra of its 500 fold dilution were typical of a stabilized bromine profile. The free and total DPD calorimetric measurements also suggested that the product was 93% oxidizing bromine compounds.

Example 4

A bench scale batch process was also performed using chlorine gas as an oxidizer. A starting solution (Solution C) was prepared by mixing 340 grams of 45% sodium bromide solution, 100 grams of soft water and 144.4 grams of solid sulfamic acid in a one-liter three neck flask. The flask was immersed in an ice-water bath to keep the solution temperature between 10° C. and 25° C. The pH of Solution C was adjusted from about pH 4.0 to about 5.0 with a sodium hydroxide solution (50% w/w). After the addition of sodium hydroxide, the temperature of Solution C was cooled to about 10° C. Chlorine gas was then bubbled into Solution C at a steady rate. While the chlorine gas was added to Solution C, the pH was maintained from about pH 4.0 to about 5.0 with a concentrated sodium hydroxide solution and the temperature was maintained from about 10° C. to about 25° C. Chlorine gas was added until the solution contained about 10.59% available chlorine according to potassium iodide-sodium thiosulfate titration. Additional sodium hydroxide solution was added to raise the product pH to about 13.5. Any mixed salts formed during the reaction were removed by filtration.

The resulting product was an amber color solution with a pH of about 13.5 and contained about 21.85% as $Br_2$ (or 9.71% as available chlorine) as measured by potassium iodide-sodium thiosulfate titration. The UV spectra of the product were typical of a stabilized bromine pattern. The free and total DPD calorimetric measurements also suggested that the product was mostly oxidizing bromine compounds (~97%).

Example 5

Another bench scale experiment was conducted by mixing 75.0 grams of a 45% sodium bromide solution with 10 grams of water in a 500 ml flask and then immersing the flask in an ice-water bath. Approximately 1 gram of sulfamic acid was added to the 500 ml flask to lower the solution pH to less than 1, and then 24.0% (weight percent as available chlorine) sodium hypochlorite solution (HyPure-N available from Olin Corporation of Cheshire, Conn.) was slowly dripped into the flask while the solution was mixed with a magnetic stir bar. When the pH increased to about 6, a small portion of sulfamic acid was added again to lower the pH back to between 2 and 3. The pH of the solution was controlled between 2 to 6 by alternating the addition of the sodium hypochlorite solution and sulfamic acid. The total amount of sulfamic acid added was 35.0 grams and the total amount of the sodium hypochlorite solution was 101.6 grams. The entire process was conducted in the solution temperature range of about 57 to 68° F. 31.75 grams of 50% sodium hydroxide solution were then slowly added to the flask while maintaining the solution temperature below 68° F.

The resulting product was am amber color solution with a pH of 13.3 and total halogen concentration of 20.75% as $Br_2$ (or 9.22% as available chlorine) as measured by potassium iodide-sodium thiosulfate titration. The UV spectra of the product were typical of a stabilized bromine pattern.

Example 6

A solution of sodium hypochlorite (CLOROX®) and two solutions of stabilized sodium hypobromite (one solution was STABREX™, available from Nalco Chemical Company of Naperville, Ill. and the other solution was prepared as described above in Example 4) were each diluted and then added to cooling water in order to achieve a one ppm total halogen residual (as chlorine). The synthetic cooling water contained 10 ppm $NH_4Cl$ and approximately $10^6$ cells/ml of mixed cooling water bacteria. Aliquots of the treated samples were extracted at 0, 0.5, 1, 2, 5, 10, 20, 30, 45, and 60 minutes into phosphate buffered dilution blanks containing a halogen neutralizer (0.05% $Na_2S_2O_3$) and then enumerated on a tryptic soy agar plate. Both solutions of stabilized sodium hypobromite were much more effective biocidally in the presence of $NH_4Cl$ than sodium hypochlorite (See Table 1 below). In addition, the efficacy of the stabilized sodium hypobromite solution prepared in Example 4 was identical to Nalco's STABREX™ product.

TABLE 1

| | $Log_{10}$ Viable Bacteria Cells/mL | | | |
|---|---|---|---|---|
| Time (Minutes) | Control | Unstabilized sodium hypochlorite (CLOROX ®) | Nalco's STABREX ™ product | Stabilized sodium hypobromite (from Example 4) |
| 0 | 6.07 | 6.07 | 6.07 | 6.07 |
| 0.5 | — | 6.05 | 6.06 | 6.07 |
| 1 | — | 6.03 | 4.78 | 4.59 |
| 2 | — | 6.07 | 2.48 | 2.48 |
| 5 | 6.02 | 6.12 | <1 | <1 |
| 10 | 6.09 | 6.03 | <1 | <1 |
| 20 | 6.07 | 5.52 | <1 | <1 |
| 30 | 6.04 | 5.08 | <1 | <1 |
| 45 | 6.09 | 3.87 | <1 | <1 |
| 60 | 6.17 | 2.00 | <1 | <1 |

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A method of making a stabilized bromine solution comprising the steps of:
   a. combining a bromine source and a stabilizer to form a mixture;
   b. adding an oxidizer to the mixture; and
   c. adding an alkaline source to the mixture to adjust the pH of the mixture to at least 13.

2. The method of claim 1 wherein the bromine source is selected from the group consisting of hydrobromic acid, bromine chloride, elemental bromine, alkali earth metal bromides and alkaline earth metal bromides.

3. The method of claim 1 wherein the stabilizer has the chemical formula R—NH—$R^1$, wherein R and $R^1$ are selected from the group consisting of $R^2$ CO, $R^2$ $SO_2$, $R^2$ $CF_2$, $R^2$ CHF, H, OH and $PO(OH)_2$, and $R^2$ is an alkyl group or an aromatic group.

4. The method of claim 1 wherein the stabilizer is selected from the group consisting of saccharin, urea, thiourea, creatinine, cyanuric acids, alkyl hydantoins, monoethanolamine, diethanolamine, organic sulfonamides, biuret, sulfamic acid, organic sulfamates and melamine.

5. The method of claim 1 wherein the stabilizer is sulfamic acid.

6. The method of claim 1 wherein the oxidizer is selected from the group consisting of chlorine gas, hypochlorous acid, hypochlorite salt, chlorite, chlorate, elemental bromine, bromine chloride, hydrogen peroxide, persulfate, permanganate and peracetic acid.

7. The method of claim 1 wherein the alkaline source is selected from the group consisting of alkali earth metal hydroxides and alkaline earth metal hydroxides.

8. The method of claim 1 wherein the alkaline source is selected from the group consisting of sodium hydroxide, lithium hydroxide, potassium hydroxide, magnesium hydroxide and calcium hydroxide.

9. The method of claim 1 wherein the molar ratio between the bromine source and the stabilizer is in the range of about 0.2 to 5.

10. The method of claim 1 wherein the molar ratio between the bromine source and the oxidizer is in the range of about 0.5 to 2.

11. The method of claim 1 wherein steps a, b and c are maintained at a temperature of less than 80° F.

12. The method of claim 1 wherein steps a, b and c are maintained in the temperature range of about 40 to 70° F.

13. The method of claim 1 wherein step b is maintained at a pH below about 7.

14. A stabilized bromine solution produced by the method of claim 1.

15. In a method for the laundering of soiled garments in which the soiled garments are washed in an aqueous media containing a detergent and a bleaching agent, the improvement comprising using as the bleaching agent the stabilized bromine solution of claim 14.

16. In a method for the manufacture of cellulosic materials in which cellulosic fibers are bleached with an oxidizing agent, the improvement comprising using as the oxidizing agent the stabilized bromine solution of claim 14.

17. In a method for the control of biofouling in a recreational water system in which an oxidizing and biocidal agent is added to control biofouling, the improvement comprising using as the oxidizing and biocidal agent the stabilized bromine solution of claim 14.

18. In a method for the control of biofouling on a hard surface in which an oxidizing and biocidal agent is applied to the surface to control biofouling on the surface, the improvement comprising using as the oxidizing and biocidal agent the stabilized bromine solution of claim 14.

19. In a method for the control of biofouling occurring on the surfaces of equipment in contact with produced oil field waters, the improvement comprising adding to the produced oil field waters an effective biofouling controlling amount of the stabilized bromine solution of claim 14.

20. A method of controlling biofouling in an aqueous system which comprises adding to the aqueous system an effective, biofouling controlling amount of the stabilized bromine solution of claim 14.

21. A method of preventing biofouling on the surfaces of equipment in contact with an industrial water system which comprises adding to the water system an effective biofouling controlling amount of a stabilized bromine solution, said solution having been prepared by the steps of:
  a. combining a bromine source and a stabilizer to form a mixture;
  b. adding an oxidizer to the mixture; and
  c. adding an alkaline source to the mixture to adjust the pH of the mixture to at least 13.

22. The method of claim 21 wherein the industrial water system is selected from the group consisting of a cooling water system, sweetwater system, gas scrubber system, air washer system, evaporative condenser, pasteurizer, produce sanitizer stream, fire protection water system and heat exchanger tube.

23. The method of claim 21 wherein the stabilized bromine solution is added to the industrial water system in an amount of from about 0.1 to about 2000 ppm as available bromine.

24. The method of claim 21 wherein the stabilized bromine solution is added to the industrial water system in an amount of from about 0.5 to about 500 ppm as available bromine.

25. A method of making a stabilized bromine solution comprising the steps of:
  a. selecting a bromine source;
  b. adding a stabilizer and an oxidizer to the bromine source to form a mixture, wherein the stabilizer and the oxidizer are alternately added to the mixture in an amount sufficient to maintain the pH of the mixture between about 0 and 6.9; and
  c. adding an alkaline source to the mixture to adjust the pH of the mixture to at least 13.

26. The method of claim 25 wherein the pH of step b is between about 3 and 6.5.

27. The method of claim 25 wherein the pH of step b is between about 4 and 6.

28. The method of claim 25 wherein the molar ratio between the bromine source and the stabilizer is in the range of about 0.2 to 5.

29. The method of claim 25 wherein the molar ratio between the bromine source and the oxidizer is in the range of about 0.5 to 2.

30. A stabilized bromine solution produced by the method of claim 25.

* * * * *